United States Patent
Saudan

(10) Patent No.: US 11,498,901 B2
(45) Date of Patent: Nov. 15, 2022

(54) HYDROGENATION OF IMINES WITH RU COMPLEXES

(71) Applicant: FIRMENICH SA, Satigny (CH)

(72) Inventor: Lionel Saudan, Satigny (CH)

(73) Assignee: FIRMENICH SA, Satigny (CH)

( * ) Notice: Subject to any disclaimer, the term of this patent is extended or adjusted under 35 U.S.C. 154(b) by 37 days.

(21) Appl. No.: 16/766,556

(22) PCT Filed: Feb. 18, 2019

(86) PCT No.: PCT/EP2019/055045
§ 371 (c)(1),
(2) Date: May 22, 2020

(87) PCT Pub. No.: WO2019/166578
PCT Pub. Date: Sep. 6, 2019

(65) Prior Publication Data
US 2021/0371382 A1 Dec. 2, 2021

(30) Foreign Application Priority Data

Mar. 2, 2018 (EP) .................................. 18159677

(51) Int. Cl.
| | | |
|---|---|---|
| *C07D 213/53* | (2006.01) | |
| *B01J 31/18* | (2006.01) | |
| *B01J 31/24* | (2006.01) | |
| *C07C 209/52* | (2006.01) | |
| *C07C 211/27* | (2006.01) | |
| *C07C 217/58* | (2006.01) | |
| *C07D 231/38* | (2006.01) | |
| *C07D 333/20* | (2006.01) | |
| *C07D 409/12* | (2006.01) | |

(52) U.S. Cl.
CPC .......... *C07D 213/53* (2013.01); *B01J 31/182* (2013.01); *B01J 31/2457* (2013.01); *C07C 209/52* (2013.01); *C07C 211/27* (2013.01); *C07C 217/58* (2013.01); *C07D 231/38* (2013.01); *C07D 333/20* (2013.01); *C07D 409/12* (2013.01); *B01J 2231/643* (2013.01); *B01J 2531/0263* (2013.01); *B01J 2531/0266* (2013.01); *B01J 2531/821* (2013.01)

(58) Field of Classification Search
CPC ...................................................... C07D 213/53
USPC ........................................................ 546/329
See application file for complete search history.

(56) References Cited

U.S. PATENT DOCUMENTS 8,614,345 B2 * 12/2013 Santoro ................. C07C 29/145
556/32

FOREIGN PATENT DOCUMENTS

| EP | 2623509 A1 | 8/2013 | | |
|---|---|---|---|---|
| WO | 0208169 A1 | 1/2002 | | |
| WO | WO 02/08169 | * | 1/2002 | ........... C07C 209/52 |
| WO | 03097571 A1 | 11/2003 | | |
| WO | WO 03/097571 | * | 11/2003 | ........... C07C 209/52 |
| WO | 2006063178 A2 | 6/2006 | | |
| WO | 2008125833 A1 | 10/2008 | | |
| WO | 2011145032 A2 | 11/2011 | | |
| WO | 2013050297 A1 | 4/2013 | | |
| WO | WO 2013/050297 | * | 4/2013 | ........... C07C 209/52 |

OTHER PUBLICATIONS

Schörgenhumer, Organic Process Research & Development 2018 22 (7), 862-870.*
Shi ACS Omega 2017, 2, 3406-3416.*
Daguenet, Organometallics 2004, 23, 4849-4857.*
Dorwald F. A. Side Reactions in Organic Synthesis, 2005, Wiley: VCH, Weinheim p. IX of Preface p. 1-15.*
International Search Report and Written Opinion for corresponding PCT/EP2019/055045 dated May 23, 2019, 12 pages.
Ryashentseva et al., Zh. Org. Khim. 1965,1, 1104-1108.

* cited by examiner

*Primary Examiner* — Nizal S Chandrakumar
(74) *Attorney, Agent, or Firm* — Armstrong Teasdale LLP

(57) ABSTRACT

Described herein are catalytic hydrogenation and the use of ruthenium complexes having a bidentate diphosphine ligand or two monodentate phosphine ligands, two carboxylate ligands, and optionally a diamine ligand in hydrogenation processes for the reduction of imines into the corresponding amines.

15 Claims, No Drawings

HYDROGENATION OF IMINES WITH RU COMPLEXES

CROSS-REFERENCE TO RELATED APPLICATIONS

This application is a U.S. National Phase Application of PCT/EP2019/055045, filed Feb. 18, 2019, which claims the benefit of priority to European Patent Application No. 18159677.6, filed Mar. 2, 2018, the entire contents of which are hereby incorporated by reference herein.

TECHNICAL FIELD

The present invention relates to the field of catalytic hydrogenation, more specifically, to the reduction of an imine into the corresponding amine in the presence of a catalytic amount of ruthenium complex having a bidentate diphosphine ligand or two monodentate phosphine ligands, two carboxylate ligands and optionally a diamine ligand.

BACKGROUND

Reduction of an imine into the corresponding amine is one of the fundamental reactions in organic chemistry, and is used in a large number of chemical processes. In general, two main types of processes are known to achieve such a transformation. Such types of processes are the following:
a) hydride processes, in which a silyl or metal hydride salt, such as NaBH$_4$, is used;
b) hydrogenation processes, in which molecular hydrogen is used.

From a practical point of view, hydrogenation processes are more attractive as they can be run using small amounts of catalyst (typically 10 to 1000 ppm relative to the substrate) and in the presence of small quantities or even in the absence of solvent. Furthermore, hydrogenation processes do not require the use of highly reactive and expensive hydrides, and do not produce important amounts of aqueous waste.

One of the mandatory and characterizing elements of hydrogenation processes is the catalyst or the catalytic system which is used to activate the molecular hydrogen in view of the reduction.

The catalytic hydrogenation of imine using homogeneous or heterogeneous catalyst has been largely described in the literature such as in WO 02/08169, WO 03/097571 or EP 2 623 509 disclosing the hydrogenation of imine in a presence of base and Ruthenium complex bearing a diamine ligand and a diphosphine ligand. However, some substrates, such as imines bearing at least one heteroaromatic ring or even two heteroaromatic rings still represent a challenging reaction sparsely reported. Actually, the presence of further heteroatom in the substrate may be detrimental to the reaction as the substrate and the product obtained may chelate to the metal center poisoning the catalytic system or a competing hydrogenation of heteroaromatic ring may occur. In particular, the few examples of the hydrogenation of thiophene-substituted imines reported only in WO 2008125833, WO 2006063178 and Zh. Org. Khim. 1965, 1, 1104-1108 using, respectively, the following heterogeneous catalysts Adam's catalyst, Pd/C and rhenium heptasulfide, reveal the challenge for this kind of substrates.

The development of useful homogeneous catalysts or catalytic systems for the hydrogenation of an imine group efficient for a large range of imine type of substrates represents still an important need in chemistry.

The present invention provides a solution to the above problem by performing said hydrogenation in a presence of a homogeneous ruthenium catalyst allowing reducing even the most challenging imine substrates. To the best of our knowledge, this process has never been reported.

SUMMARY OF THE INVENTION

Surprisingly, it has now been discovered that the imines comprising a heterocyclic group may be easily reduced under hydrogenation conditions using a homogeneous catalyst and in the absence of any additive.

So, a first object of the present invention is a process for the reduction by hydrogenation, using molecular H$_2$, of a C$_5$-C$_{20}$ substrate of formula

(I)

wherein R$^a$ and R$^c$ represent, independently from each other, a hydrogen atom or a C$_1$-C$_{15}$ hydrocarbon group optionally comprising one to three oxygen atoms and/or one to two nitrogen atoms and/or one sulphur or halogen atom; R$^b$ represent a C$_1$-C$_{15}$ hydrocarbon group optionally comprising one to three oxygen atoms and/or one to two nitrogen atoms and/or one sulphur or halogen atom, a hydrogen atom, a SO$_2$R$^{b'}$, a OR$^{b'''}$ or a POR$^{b'}_2$ group wherein R$^{b'}$ represents a C$_1$-C$_6$ alkyl group or a phenyl or tolyl group and R$^{b'''}$ represents a hydrogen atom, a C$_1$-C$_6$ alkyl group or a phenyl or tolyl group; or R$^a$ and R$^c$ represent, when taken together, a C$_1$-C$_{10}$ alkanediyl or alkenediyl group; provided than at least one R$^a$, R$^b$ or R$^c$ is not a hydrogen atom;
into the corresponding amine, characterized in that said process is carried out in the presence of at least one catalyst or pre-catalyst of formula

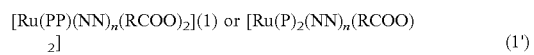

wherein n is 0 or 1; PP represents a C$_5$-C$_{50}$ bidentate ligand wherein the coordinating groups are two phosphino groups; P represents a C$_3$-C$_{50}$ monodentate ligand; NN represents a C$_2$-C$_{20}$ bidentate ligand wherein the coordinating atoms are two nitrogen atoms; and
each R represents, simultaneously or independently, a hydrogen atom, a C$_1$-C$_{12}$ linear hydrocarbon group or a branched or cyclic C$_3$-C$_{12}$ hydrocarbon group and said hydrocarbon group comprises optionally one to five heteroatoms selected amongst halogen, oxygen and nitrogen atoms.

Description of the Invention

The present invention relates to a process for the reduction by hydrogenation, using molecular H$_2$, of a C$_5$-C$_{20}$ substrate containing an imine functional groups into the corresponding amine, characterized in that said process is carried out in the presence of at least one catalyst or pre-catalyst in the form of a ruthenium complex having a bidentate diphosphine ligand or two monodentate phosphine ligands and two carboxylate ligands.

Said process allows reducing even the most challenging thiophene-substituted imines using a homogeneous ruthenium catalyst. In addition, said process is carried in the absence of any acidic or basic additive making it particularly interesting for sensitive substrates.

As well understood by a person skilled in the art, by "bidentate" it is understood that said ligand coordinates the Ru metal with two atoms (e.g. two P).

So a first object of the present invention is a process for the reduction by hydrogenation, using molecular $H_2$, of a $C_5$-$C_{20}$ substrate of formula

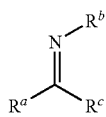

(I)

wherein $R^a$ and $R^c$ represent, independently from each other, a hydrogen atom or a $C_1$-$C_{15}$ hydrocarbon group optionally comprising one to three oxygen atoms and/or one to two nitrogen atoms and/or one sulphur or halogen atom; $R^b$ represent a $C_1$-$C_{15}$ hydrocarbon group optionally comprising one to three oxygen atoms and/or one to two nitrogen atoms and/or one sulphur or halogen atom, a hydrogen atom, a $SO_2R^{b'}$, a $OR^{b''}$ or a $POR^{b'}_2$ group wherein $R^{b'}$ represents a $C_1$-$C_6$ alkyl group or a phenyl or tolyl group and $R^{b''}$ represents a hydrogen atom, a $C_1$-$C_6$ alkyl group or a phenyl or tolyl group; or $R^a$ and $R^c$ represent, when taken together, a $C_1$-$C_{10}$ alkanediyl or alkenediyl group; provided than at least one $R^a$, $R^b$ or $R^c$ is not a hydrogen atom;

into the corresponding amine, characterized in that said process is carried out in the presence of at least one catalyst or pre-catalyst of formula

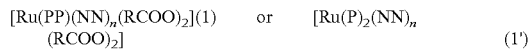

(1')

wherein n is 0 or 1; PP represents a $C_5$-$C_{50}$ bidentate ligand wherein the coordinating groups are two phosphino groups; P represents a $C_3$-$C_{50}$ monodentate ligand;

NN represents a $C_2$-$C_{20}$ bidentate ligand wherein the coordinating atoms are two nitrogen atoms; and each R represents, simultaneously or independently, a hydrogen atom, a $C_1$-$C_{12}$ linear hydrocarbon group or a branched or cyclic $C_3$-$C_{12}$ hydrocarbon group and said hydrocarbon group comprises optionally one to five heteroatoms selected amongst halogen, oxygen and nitrogen atoms.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies. In all the embodiments of the invention, when it is mentioned that the hydrocarbon group may optionally comprises heteroatom such as oxygen atoms, nitrogen atoms or sulphur atoms, it is meant that at least one hydrogen atom of the hydrocarbon group may be substituted by a heteroatom and/or that carbon atom of the hydrocarbon chain may be substituted/replaced by a heteroatom; i.e. the hydrocarbon may comprise as substituent or, as part of the chain, functional group such as ether, thiol, amine, ester, amide.

The corresponding amine (I-a) provided by the invention's process; i.e hydrogenation of imine of formula (I), is of formula

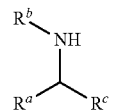

(I-a)

wherein $R^a$, $R^b$ and $R^c$ have the same meaning as defined as in formula (I).

According to any one of the above embodiments of the invention, the compound of formula (I) may be in the form of any one of its stereoisomers or as a mixture thereof. For the sake of clarity, by the expression "any one of its stereoisomers or as a mixture thereof", or the similar, it is meant the normal meaning understood by a person skilled in the art, i.e. that the compounds of formula (I) can be a pure or be in the form of a mixture of enantiomers or diastereoisomers.

According to any one of the above embodiments of the invention, said compound of formula (I) can be in the form of its E or Z isomer or of a mixture thereof, e.g. the invention comprises compositions of matter consisting of one or more compounds of formula (I), having the same chemical structure but differing by the configuration of the imine double bond. In particular, compound (I) can be in the form of a mixture consisting of isomer E and Z and wherein said isomer E represent at least 0.5% of the total mixture, or even at least 50% of the total mixture, or even at least 75% (i.e a mixture E/Z comprised between 75/25 and 100/0).

According to any one of the above embodiments of the invention, the compound of formula (I) may be generated in situ by the condensation between a carbonyl compound of formula $(R^a)(R^c)C(=O)$ and an amine of formula $R^bNH_2$.

According to any one of the above embodiments of the invention, $R^a$, $R^b$ and $R^c$ may represent a hydrogen atom, a $C_1$-$C_{10}$ alkyl, alkenyl, alkanedienyl, aryl, heterocyclic, heteroarylalkyl or arylalkyl group optionally substituted by a hydroxyl group, a halogen atom, a $C_{1-6}$ alkyl group or a $C_{1-6}$ alkoxy group.

According to any one of the above embodiments of the invention, $R^a$, $R^b$ and $R^c$ may represent a hydrogen atom, a $C_1$-$C_{10}$ alkyl, alkenyl, alkanedienyl, aryl, heterocyclic or arylalkyl group optionally substituted by a hydroxyl group, a $C_{1-6}$ alkyl group or a $C_{1-6}$ alkoxy group.

According to any one of the above embodiments of the invention, $R^a$, $R^b$ and $R^c$ may represent, independently from each other, a hydrogen atom, a $C_1$-$C_{10}$ linear alkyl group, a $C_2$-$C_{10}$ linear alkenyl group, a $C_3$-$C_{10}$ linear, branched or cyclic alkyl or alkenyl group, a $C_4$-$C_{10}$ linear, branched or cyclic alkadienyl group, a $C_{3-8}$ aryl, a $C_{2-8}$ heterocyclic or a $C_{6-12}$ arylalkyl group optionally substituted by a hydroxyl group, a $C_{1-6}$ alkyl group or a $C_{1-6}$ alkoxy group; or $R^a$ and $R^c$ represent, when taken together, a $C_1$-$C_{10}$ alkanediyl or alkenediyl group; provided than at least one $R^a$, $R^b$ or $R^c$ is not a hydrogen atom.

The expression "a linear, branched or cyclic alkyl, alkenyl or alkadienyl group" or similar designated that said $R^a$, $R^b$ and $R^c$ can be in the form of, e.g., a linear alkyl group or can also be in the form of a mixture of said type of groups, e.g. a specific $R^a$ may comprise a branched alkenyl, a (poly) cyclic alkyl and a linear alkyl moiety, unless a specific limitation to only one type is mentioned. Similarly, in all the below embodiments of the invention, when a group is mentioned as being an alkenyl or alkadienyl, it is meant that said group comprises one or two carbon-carbon double bonds which can be conjugated or not with the imine group or between them, in the case of alkadienyl. Similarly, in all the below embodiments of the invention, when a group is mentioned as being in the form of more than one type of topology (e.g. linear, cyclic or branched) and/or unsaturation (e.g. alkyl or alkenyl) it is meant also a group which may comprise moieties having any one of said topologies or unsaturations, as explained above. Similarly, in all the below embodiments of the invention, when a group is mentioned as being in the form of one type of unsaturation, (e.g. alkyl), it is meant that said group can be in any type of topology (e.g. linear, cyclic or branched) or having several moieties with various topologies.

The term "heterocyclic" or similar have the normal meaning in the art; i.e. an aromatic ring comprising at least one heteroatom such as oxygen, nitrogen or sulphur atom. Typical examples of heterocyclic group include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole or xanthene.

The term "arylalkyl" have the normal meaning in the art; i.e. an acyclic alkyl group wherein one hydrogen atom is replaced with an aryl group.

The term "heteroarylalkyl" have the normal meaning in the art; i.e. an acyclic alkyl group wherein one hydrogen atom is replaced with an heterocyclic group.

According to any one of the invention's embodiments, the substrate is an imine that will provide an amine that is useful in the pharmaceutical, agrochemical, flavor or perfumery industry as final product or as an intermediate. Particularly preferred substrate is an imine that will provide an amine which is useful in the flavor and fragrance industry as final product or as an intermediate.

According to any one of the invention's embodiments, the substrate is a $C_5$-$C_{15}$ compound of formula (I).

According to any one of the invention's embodiments, the substrate is of formula

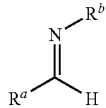

(I')

wherein $R^a$ and $R^b$ have the same meaning than above.

According to any one of the invention's embodiments, $R^a$ and $R^b$ may represent, independently from each other, a $C_1$-$C_8$ linear alkyl group, a $C_2$-$C_8$ linear alkenyl group, a $C_3$-$C_8$ linear, branched or cyclic alkyl or alkenyl group, a $C_4$-$C_8$ linear, branched or cyclic alkadienyl group, or a $C_{3-6}$ aryl, a $C_{2-6}$ heterocyclic $C_{6-8}$ heteroarylalkyl or a $C_{6-8}$ arylalkyl group optionally substituted by a hydroxyl group, a halogen atom, a $C_{1-3}$ alkyl group or a $C_{1-3}$ alkoxy group.

According to any one of the invention's embodiments, $R^a$ and $R^b$ may represent, independently from each other, a $C_1$-$C_8$ linear alkyl group, a $C_2$-$C_8$ linear alkenyl group, a $C_3$-$C_8$ linear, branched or cyclic alkyl or alkenyl group, a $C_4$-$C_8$ linear, branched or cyclic alkadienyl group, or a $C_{3-6}$ aryl, a $C_{2-6}$ heterocyclic or a $C_{6-8}$ arylalkyl group optionally substituted by a hydroxyl group, a $C_{1-3}$ alkyl group or a $C_{1-3}$ alkoxy group. Preferably, $R^a$ and $R^b$ may represent, independently from each other, a $C_3$-$C_8$ cyclic alkyl group, a $C_{3-6}$ aryl, a $C_{2-6}$ heterocyclic or a $C_{6-8}$ arylalkyl group optionally substituted by a hydroxyl group, a $C_{1-3}$ alkyl group or a $C_{1-3}$ alkoxy group group. Preferably, $R^a$ and $R^b$ may represent, independently from each other, a $C_{3-6}$ aryl, a $C_{2-6}$ heterocyclic or a $C_{6-8}$ arylalkyl group optionally substituted by a hydroxyl group, a $C_{1-3}$ alkyl group or a $C_{1-3}$ alkoxy group. Preferably, $R^a$ or $R^b$ may represent a $C_{2-6}$ heterocyclic group optionally substituted by a hydroxyl group, a $C_{1-3}$ alkyl group or a $C_{1-3}$ alkoxy group and the other may represent a $C_1$-$C_8$ linear alkyl group, a $C_2$-$C_8$ linear alkenyl group, a $C_3$-$C_8$ linear, branched or cyclic alkyl or alkenyl group, a $C_4$-$C_8$ linear, branched or cyclic alkadienyl group or a $C_{3-6}$ aryl, a $C_{2-6}$ heterocyclic or a $C_{6-8}$ arylalkyl group optionally substituted by a hydroxyl group, a $C_{1-3}$ alkyl group or a $C_{1-3}$ alkoxy group. Even more preferably, $R^a$ and $R^b$ may represent, independently from each other, a $C_{2-6}$ heterocyclic group optionally substituted by a hydroxyl group, a $C_{1-3}$ alkyl group or a $C_{1-3}$ alkoxy group. Preferably, $R^a$ and $R^b$ may represent, independently from each other, a $C_{2-6}$ heterocyclic group comprising from 1 to 3 heteroatoms selected from nitrogen, oxygen and sulphur atom, optionally substituted by one or two $C_{1-3}$ alkyl groups. Preferably, $R^a$ and $R^b$ represent, independently from each other a $C_{3-6}$ heterocyclic group comprising from 1 to 3 heteroatoms selected from nitrogen, oxygen and sulphur. Even more preferably, $R^a$ and $R^b$ represent, independently from each other a $C_{3-5}$ heterocyclic group comprising from 1 to 3 heteroatoms selected from nitrogen, oxygen and sulphur. Even more preferably, $R^a$ and $R^b$ represent, independently from each other a $C_{3-5}$ heterocyclic group comprising from 1 to 3 heteroatoms selected from nitrogen and sulphur.

According to any one of the above embodiments, $R^b$ represents a or a $C_{3-6}$ aryl, a $C_{6-8}$ arylalkyl or a $C_{3-5}$ heterocyclic group comprising from one or two nitrogen atoms, one nitrogen atom and one sulphur atom or one nitrogen atom and one oxygen atom. Preferably, $R^b$ represents a phenyl or benzyl group or a $C_{3-5}$ heterocyclic group comprising from one or two nitrogen atoms, one nitrogen atom and one sulphur atom or one nitrogen atom and one oxygen atom. Preferably, $R^b$ represents a pyrazolyl group.

According to any one of the above embodiments, $R^a$ represents a $C_{3-5}$ heterocyclic group comprising from one or two sulphur atoms, one oxygen atom, one nitrogen atom or one nitrogen atom and one sulphur atom. Preferably, $R^a$ represents a thiophenyl group.

Non-limiting examples of substrates of formula (I) may include N-(1H-pyrazol-5-yl)-1-(thiophen-2-yl)methanimine, N-(4-methoxyphenethyl)-1-(thiophen-2-yl)methanimine, N-benzyl-1-(thiophen-2-yl)methanimine, N-benzyl- 1-(p-tolyl)methanimine, N-benzyl-1-(2-methoxyphenyl) methanimine or N-(1H-pyrazol-5-yl)-1-(p-tolyl) methanimine, N-phenyl-1-(thiophen-2-yl)methanimine, N-benzyl-1-(thiophen-2-yl)methanimine, N-phenyl-1-(p-tolyl)methanimine, N-(4-methoxyphenyl)-1-phenylmethanimine, N-cyclohexyl-1-(p-tolyl)methanimine, N-(4-fluorophenyl)-1-(p-tolyl)methanimine, N-(4-methoxyphenyl)-1-(p-tolyl)methanimine, N-(2,4-dimethylphenyl)-1-(p-tolyl)methanimine, N-(pyridin-4-ylmethyl)-1-(p-tolyl)methanimine, 1-(thiophen-2-yl)-N-(thiophen-2-ylmethyl) methanimine.

In the present invention, the presence of acidic or basic additive is avoided. This is an advantage, since it allows significant increases in yields for the production of amines from acid- and/or base-sensitive imines Therefore, according to anyone of the invention's embodiments, the substrate is an acid and/or base-sensitive compound.

According to any embodiment of the invention, the process of the invention is performed in absence of base.

According to any one of the invention's embodiments, the ruthenium complex can be of the general formula $$[Ru(PP)(NN)_n(RCOO)_2] \quad (1)$$

wherein n is 0 or 1; PP represents a $C_5$-$C_{50}$ bidentate ligand wherein the coordinating groups are two phosphino groups; NN represents a $C_2$-$C_{20}$ bidentate ligand wherein the coordinating groups are two amino groups; and
each R represents, simultaneously or independently, a hydrogen atom, a $C_1$-$C_{12}$ linear hydrocarbon group or a branched or cyclic $C_3$-$C_{12}$ hydrocarbon group and said hydrocarbon group is optionally comprising one to five heteroatoms selected amongst halogen, oxygen and nitrogen atoms.

According to any one of the invention's embodiments, in formula (1), each R may represent, simultaneously or independently:
a $C_{1-12}$ linear alkyl group
   optionally substituted by a $C_{3-6}$ cycloalkyl or cycloalkenylone group or a phenyl group optionally substituted by one to five halogen atoms and/or $C_{1-4}$ alkoxyl groups; and
   optionally comprising one OH, amino or ether functional group or at least one halogen atom;
or
a $C_{3-12}$ branched or cyclic alkyl group
   optionally substituted by one phenyl group optionally substituted by one to five halogen atoms and/or $C_{1-4}$ alkyl or alkoxyl groups; and
   optionally comprising one OH, amino or ether functional group or at least one halogen atom;
or
a phenyl group optionally substituted by one to three, or five, halogen atoms and/or $C_{1-4}$ alkyl or alkoxyl groups and/or nitro groups.

According to any one of the invention's embodiments, in formula (1), each R may represent, simultaneously or independently:
a $C_{3-12}$ branched or cyclic alkyl group
   optionally substituted by one phenyl group optionally substituted by one to five halogen atoms and/or $C_{1-4}$ alkyl or alkoxyl groups; and
   optionally comprising one OH, amino or ether functional group;
or
a phenyl group optionally substituted by one to three, or five, halogen atoms and/or $C_{1-4}$ alkyl or alkoxyl groups and/or nitro groups.

According to a particular embodiment of the formula (1), said R group may represent
   a branched $C_{3-10}$ alkyl group comprising in the α position a tertiary or quaternary carbon atom and/or in the β position a quaternary carbon atom and also optionally comprising one OH, one ether functional group or one phenyl group, the phenyl group being optionally substituted by one or two halogen atoms and/or by $C_{1-4}$ alkyl or alkoxyl groups;
   a $C_2$ alkyl group comprising in the a position one OH or one ether functional group; or
   a phenyl group optionally substituted by one, two or three halogen atoms and/or by $C_{1-4}$ alkyl or alkoxyl groups and/or nitro groups.

According to a particular embodiment of the formula (1), said R group may represent
   a branched $C_{3-10}$ alkyl group comprising in the α position a tertiary or quaternary carbon atom and/or in the β position a quaternary carbon atom; or
   a phenyl group optionally substituted by one, two or three halogen atoms and/or by $C_{1-4}$ alkyl or alkoxyl groups and/or nitro groups.

For the sake of clarity, by the expression "a position" it is meant the usual meaning in the art, i.e. the carbon atom directly bound to the COO moiety of the group RCOO. Similarly by the expression "β position" it is meant a carbon atom directly bound to the a position. For the sake of clarity, by the expression "group branched or cyclic" it is meant a group which is not linear, i.e. a cyclohexyl, a iso-propyl, or $ClCH_2$ but not $CH_2CH_3$ or $CCl_3$, and it is also clear that the branching may be due to one or several carbon atoms or an optional functional group, which may be part of a cycle or not.

As non-limiting examples of suitable RCOO group of (I), one may cite the isobutyrate, pivalate, ′Bu-acetate, trifluoroacetate, 2-Et-hexanoate, cyclohexanecarboxylate, picolinate, cinnamate, benzoate, 4-Me-benzoate, 4-OMe-benzoate, 3,5-dichloro-benzoate, 2,4-dichloro-benzoate, isovalerate, adamantate or sec-butyrate.

According to any one of the invention's embodiments, the bidentate NN ligand is a compound of formula (B)

$$R^1\underset{(R^1)_{a'}}{\overset{}{\text{N}}}\overset{R^2}{\underset{}{\text{C}}}\left(Q\right)_a\overset{R^2}{\underset{R^3}{\text{C}}}\overset{}{\underset{R^1}{\text{N}}}R^1$$

wherein a and a', simultaneously or independently, represent 0 or 1 (when a' is 0 then the nitrogen atom is part of an aromatic heterocycle);
the $R^1$, taken separately, represent, simultaneously or independently, a hydrogen atom or a $C_{1-6}$ linear, branched or cyclic alkyl group optionally substituted or a phenyl or a benzyl group optionally substituted; two $R^1$, taken together, may form a saturated heterocycle containing 3 to 7 atoms and including the atoms to which said $R^1$ are bonded, said heterocycle being optionally substituted;
$R^2$ and $R^3$, taken separately, represent, simultaneously or independently, a hydrogen atom, a $C_{1-6}$ linear, branched alkyl group optionally substituted or a $C_{6-10}$ aromatic group optionally substituted; a $R^1$ and an adjacent $R^2$, taken together, may form a saturated or unsaturated heterocycle containing 5 to 8 atoms and including the atoms to which said $R^1$ and $R^2$ are bonded, and optionally containing one additional nitrogen or oxygen atom; two $R^2$, taken together, may form a saturated or unsaturated ring having 5 to 8 atoms and including the carbon atoms to which said two $R^2$ groups are bonded, said ring optionally containing one additional nitrogen and/or oxygen atom; and Q represents a group of formula

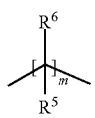
(i)

wherein m is 1 or 2, and $R^5$ and $R^6$ represent, simultaneously or independently, a hydrogen atom, a $C_{1-6}$ linear, branched or cyclic alkyl group optionally substituted or a $C_{6-10}$ aromatic group optionally substituted; two distinct $R^6$ and/or $R^5$ groups, taken together, may form a $C_{3-8}$ saturated ring optionally substituted, including the atoms to which said $R^6$ and/or $R^5$ groups are bonded, and optionally containing one or two additional nitrogen or oxygen atoms.

According to an embodiment, by "aromatic group or ring" it is meant a phenyl or naphthyl group.

As mentioned above, in said ligand (B) the atoms which may coordinate the Ru atom are the two N atoms bearing the $R^1$ groups. Therefore, it is also understood that whenever said $R^1$, $R^2$, $R^3$, $R^5$, $R^6$ or any other group comprises heteroatoms such as N or O, said heteroatoms are not coordinating.

Possible optional substituents of $R^1$, $R^2$, $R^3$, $R^5$, $R^6$ are one, two, three or four groups selected amongst i) halogens (in particular when said substituents are on aromatic moieties), ii) $C_{1-6}$ alkoxy, alkyl, alkenyl, or iii) a benzyl group or a fused or non-fused phenyl group, said group being optionally substituted by one, two or three halogen, $C_{1-8}$ alkyl, alkoxy, amino, nitro, ester, sulfonate or halo- or perhalo-hydrocarbon groups.

For the sake of clarity, and as mentioned above, in any one of the embodiments of the present invention, whenever two groups of formula (B) are taken together to form a cycle or ring, said cycle or ring can be a mono or bi-cyclic group.

According to any one of the invention's embodiments of said bidentate NN ligand, each $R^1$, simultaneously or independently, represents a hydrogen atom or a $C_{1-4}$ linear or branched alkyl group. Preferably, $R^1$, simultaneously or independently, represents a hydrogen atom or a methyl or ethyl group.

According to any one of the invention's embodiments of said bidentate (NN) ligand, at least one $R^1$ represents a hydrogen atom, or even at least two $R^1$ represents a hydrogen atom, or even the four $R^1$ represent a hydrogen atom.

According to any one of the invention's embodiments of said bidentate NN ligand, $R^2$ and $R^3$, taken separately, represent, simultaneously or independently, a hydrogen atom, a $C_{1-4}$ linear or branched alkyl group optionally substituted or a phenyl group optionally substituted; a $R^1$ and an adjacent $R^2$, taken together, may form a saturated or unsaturated heterocycle containing 5 or 6 atoms and including the atoms to which said $R^1$ and $R^2$ are bonded and optionally containing one additional oxygen atom; two $R^2$, taken together, may form a saturated or unsaturated ring having 5 or 6 atoms and including the atoms to which said $R^2$ or $R^3$ groups are bonded, said ring being optionally substituted and optionally containing one additional oxygen atom.

According to any one of the invention's embodiments of said bidentate NN ligand, $R^2$ and $R^3$, taken separately, represent, simultaneously or independently, a hydrogen atom, a $C_{1-4}$ linear or branched alkyl group or a phenyl group; a $R^1$ and an adjacent $R^2$, taken together, may form a saturated or aromatic heterocycle containing 6 atoms and including the atoms to which said $R^1$ and $R^2$ are bonded; two $R^2$, taken together, may form a saturated or unsaturated ring having 5 or 6 atoms and including the atoms to which said two $R^2$ groups are bonded.

According to any one of the invention's embodiments of said bidentate NN ligand, said Q represents a group of formula

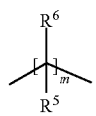
(i)

wherein m is 1 or 2, and $R^5$ and $R^6$ represent, simultaneously or independently, a hydrogen atom, a $C_{1-4}$ linear or branched alkyl group or a phenyl group optionally substituted.

According to any one of the invention's embodiments of said bidentate NN ligand, said $R^5$ and $R^6$ represent, simultaneously or independently, a hydrogen atom, or a $C_{1-4}$ linear alkyl group.

According to a particular embodiment of the invention, said Q can be a group of formula (i) wherein m is 1 or 2, $R^5$ is a hydrogen atom and $R^6$ is as defined above.

According to any one of the invention's embodiments of said bidentate NN ligand, said ligand NN is represented by formula

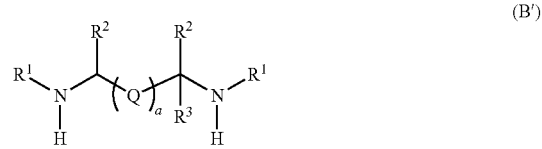
(B')

wherein a represents 0 or 1;

each $R^1$, simultaneously or independently, represents a hydrogen atom or a $C_{1-4}$ linear or branched alkyl group or a benzyl group optionally substituted;

$R^2$ and $R^3$, taken separately, represent, simultaneously or independently, a hydrogen atom, a $C_{1-4}$ linear or branched alkyl group optionally substituted or a phenyl group optionally substituted; a $R^1$ and an adjacent $R^2$, taken together, may form a saturated heterocycle containing 6 atoms and including the atoms to which said $R^1$ and $R^2$ are bonded, and being optionally substituted; two $R^2$ taken together, may form a saturated ring having 5 to 6 atoms and including the carbon atoms to which said $R^2$ groups are bonded; and Q represents a group of formula

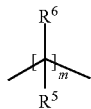
(i)

wherein m is 1 or 2, and
$R^5$ and $R^6$ represent, simultaneously or independently, a hydrogen atom, a $C_{1-4}$ linear or branched alkyl group or a phenyl group optionally substituted.

According to a particular aspect of the above embodiment, said ligand NN of formula (B') is one wherein
a represents 0 or 1;
each $R^1$, simultaneously or independently, represents a hydrogen atom or a $C_{1-4}$ alkyl group;
$R^2$ and $R^3$, taken separately, represent, simultaneously or independently, a hydrogen atom; two $R^2$ taken together, may form a saturated ring having 5 to 6 atoms and including the carbon atoms to which said $R^2$ groups are bonded; and
Q represents a group of formula

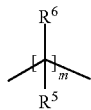
(i)

wherein m is 1 or 2, and
$R^5$ and $R^6$ represent, simultaneously or independently, a hydrogen atom, a $C_{1-4}$ linear alkyl group.

According to any one of the invention's embodiments, said ligand NN is represented by formula

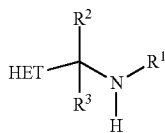
(B″)

wherein $R^1$ represents a hydrogen atom or a $C_{1-4}$ linear or branched alkyl group;
$R^2$ and $R^3$, taken separately, represent, simultaneously or independently, a hydrogen atom, a $C_{1-4}$ linear or branched alkyl group; and
HET represents a 2-pyridinyl group optionally substituted by one, two or three $C_{1-4}$ linear or branched alkyl groups or by a benzyl group or a fused or non-fused phenyl or indanyl group, said group being optionally substituted by one, two or three halogen, $C_{1-4}$ alkyl, alkoxy, amino, nitro, ester or sulfonate groups, such as a 2-pyridyl, 2-quinolinyl or a methyl-2-pyridinyl.

According to a particular embodiment of formula (B″), $R^1$ represents, a hydrogen atom.

According to a particular embodiment of formula (B″), $R^2$ and $R^3$, taken separately, represent, simultaneously or independently, a hydrogen atom.

According to a particular embodiment of formula (B″), HET represents a 2-pyridinyl group optionally substituted by one, two or three $C_{1-4}$ linear or branched alkyl groups or a fused or non-fused phenyl group, such as a 2-pyridyl, 2-quinolinyl or a methyl-2-pyridinyl.

According to any one of the invention's embodiments of said bidentate NN ligand, the possible substituents of $R^1$, $R^2$, $R^3$, $R^5$ or $R^6$ of formulae (B), (B') or (B″) are one or two i) halogens, ii) $C_{1-5}$ alkyl or alkoxy groups, or iii) a fused or non-fused phenyl group, said group being optionally substituted by one, two or three halogen, $C_{1-4}$ alkyl or alkoxy groups.

As non-limiting examples of N-N ligands one can cite the ones in the following Scheme (A):

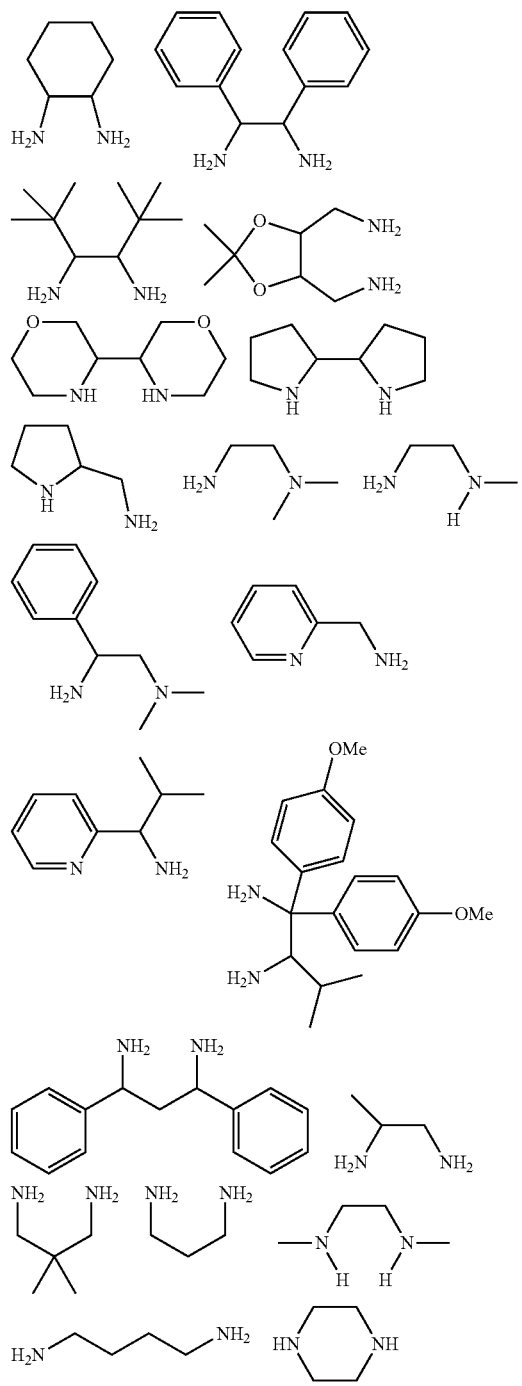

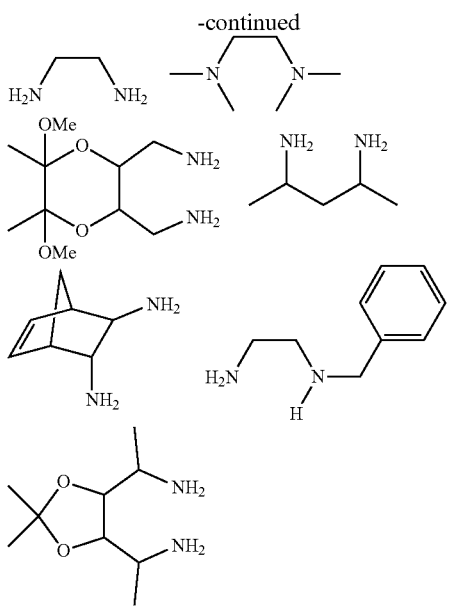

said compounds being in an optically active form or in a racemic form, if applicable.

Preferably, ligand (NN) may be selected from the group consisting of ethane-1,2-diamine, N,N-dimethylethane-1,2-diamine, N,N,N',N'-tetramethylethane-1,2-diamine, 1,2-diphenylethane-1,2-diamine, (1R,2R)-1,2-diphenylethane-1,2-diamine, cyclohexane-1,2-diamine, (1R,2R)-cyclohexane-1,2-diamine, propane-1,3-diamine and pyridin-2-ylmethanamine.

According to any one of the embodiments of the present invention, the bidentate ligand (PP) can be a compound of formula

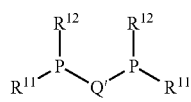

(C)

wherein $R^{11}$ and $R^{12}$, when taken separately, represent, simultaneously or independently, a $C_{1-6}$ linear alkyl group optionally substituted, a $C_{3-6}$ branched or cyclic alkyl group optionally substituted or a $C_{6-10}$ aromatic group optionally substituted; and
Q' represents
  a group of formula

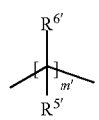

(i')

wherein m' is 1, 2, 3 or 4 and
$R^{5'}$ and $R^{6'}$ represent, simultaneously or independently, a hydrogen atom, a $C_{1-6}$ linear or branched alkyl group optionally substituted or a $C_{6-10}$ aromatic group optionally substituted; two distinct $R^{6'}$ and/or $R^{5'}$ groups, taken together, may form a $C_3$ to $C_8$ saturated or unsaturated ring optionally substituted, including the atoms to which said $R^{6'}$ and/or $R^{5'}$ groups are bonded, and optionally containing one or two additional nitrogen or oxygen atoms; or
  a $C_{10}$-$C_{16}$ metallocenediyl, a 2,2'-diphenyl, a 1,1'-binaphthalene-2,2'-diyl, a benzenediyl, a naphthalenediyl, 2,3-bicyclo[2:2:1]hept-5-enediyl, 4,6-phenoxazinediyl, 4,5-(9,9-dimethyl)-xanthenediyl, 4,6-10H-phenoxazinediyl, 2,2'-(oxybis(2,1-phenylene)) or bis(phen-2-yl) ether group optionally substituted.

As mentioned above, according to a particular embodiment of the invention, by "aromatic group or ring" for (PP) it is also meant a phenyl or naphthyl derivative.

As mentioned above, in said ligand (C) the atoms which may coordinate the Ru atom are the P atoms of the $PR^{11}R^{12}$ groups. Therefore, it is also understood that whenever said $R^{5'}$, $R^{6'}$, $R^{11}$, $R^{12}$, Q' or any other group comprises heteroatoms such as N or O, said heteroatoms are not coordinating.

Possible substituents of $R^{5'}$, $R^{6'}$, $R^{11}$ and $R^{12}$ are one to five halogens (in particular when said substituents are on aromatic moieties), or one, two or three i) $C_{1-6}$ linear or branched alkyl, alkoxy groups or halo- or perhalo-hydrocarbon, amine groups, ii) $COOR^h$ wherein $R^h$ is a $C_{1-6}$ linear, branched or cyclic alkyl group, iii) $NO_2$ group, or iv) a benzyl group or a fused or non-fused phenyl group, said group being optionally substituted by one, two or three halogen, $C_{1-8}$ alkyl, alkoxy, amino, nitro, ester, sulfonate or halo- or perhalo-hydrocarbon groups. By "halo- or perhalo-hydrocarbon" it is meant groups such as $CF_3$ or $CClH_2$ for instance.

For the sake of clarity, and as mentioned above, in any one of the embodiments of the present invention, whenever two groups of formula (C) are taken together to form a cycle or ring, said cycle or ring can be a mono or bi-cyclic group.

According to any one of the invention's embodiments of said bidentate PP ligand, $R^{11}$ and $R^{12}$, when taken separately, represent, simultaneously or independently, a $C_{3-6}$ branched or cyclic alkyl group or a $C_{6-10}$ aromatic group, or preferably a phenyl group, optionally substituted.

According to any one of the invention's embodiments of said bidentate PP ligand, $R^{11}$ and $R^{12}$ represent each, simultaneously or independently, a $C_{3-6}$ branched or cyclic alkyl group or a phenyl group optionally substituted. Preferably, $R^{11}$ and $R^{12}$ represent each, simultaneously or independently a isopropyl, a cyclohexyl or a phenyl group.

According to any one of the invention's embodiments of said bidentate PP ligand, Q' represents
  a group of formula

(i')

wherein m' is 1, 2, 3 or 4 and
$R^{5'}$ and $R^{6'}$ represent, simultaneously or independently, a hydrogen atom, a $C_{1-4}$ linear or branched alkyl group or a $C_{6-10}$ aromatic group, or preferably a phenyl group, optionally substituted; two distinct $R^{6'}$ and/or $R^{5'}$ groups, taken together, may form a $C_{4-6}$ saturated or unsaturated ring optionally substituted, including the atoms to which said $R^{6'}$ and/or $R^{5'}$ groups are bonded; or
  a $C_{10}$-$C_{16}$ metallocenediyl, a 2,2'-diphenyl a benzenediyl, a naphthalenediyl, a 1,1'-binaphthalene-2,2'-diyl, 2,3-bicyclo [2:2:1]hept-5-enediyl, 4,6-phenox azinediyl, 4,5-(9,9-dimethyl)-xanthenediyl4,6-10H-phenoxazinediyl, 2,2'-(oxybis(2,1-phenylene)) or bis(phen-2-yl) ether group optionally substituted.

According to any one of the invention's embodiments of said bidentate PP ligand, Q' may represent a linear $C_{1-4}$ alkanediyl radical, a 1,2- or 1,1'-$C_{10-12}$ metallocenediyl, a 2,2'-diphenyl, a 1,2-benzenediyl, a 1,1'-binaphthalene-2,2'-diyl, or a 1,8- or 1,2-naphthalenediyl, 4,6-10H-phenox azinediyl or 2,2'-(oxybis(2,1-phenylene)) group optionally substituted. Preferably, Q' may represent a linear $C_{1-4}$ alkanediyl radical, a 1,2- or 1,1'-$C_{10-12}$ metallocenediyl group.

According to a particular embodiment of the invention, said PP ligand is a compound of formula (C) wherein $R^{11}$ and $R^{12}$ represent, simultaneously or independently, a $C_{3-6}$ branched or cyclic alkyl group or a phenyl group optionally substituted; and Q' represents a $C_1$-$C_4$ alkanediyl radical optionally substituted, a $C_{10}$-$C_{12}$ ferrocenediyl, a 2,2'-diphenyl, a 1,1'-binaphthalene-2,2'-diyl, a 1,2-benzenediyl or a naphthalenediyl group.

According to any one of the invention's embodiments of said bidentate PP ligand, said ligand is a compound wherein one, two or three of the Q', $R^{11}$ and $R^{12}$ groups are satured groups (i.e. alkyl or alkanediyl groups). In particular Q' represents a $C_1$-$C_4$ alkanediyl radical optionally substituted and/or $R^{11}$ and $R^{12}$ a branched or cyclic alkyl group.

Possible substituents of said $R^{11}$ or $R^{12}$ are as described above for $R^1$ to $R^6$. Possible substituents of said Q' are as described above for Q.

As non-limiting examples of PP ligands, one can cite the ones in the following Scheme (B):

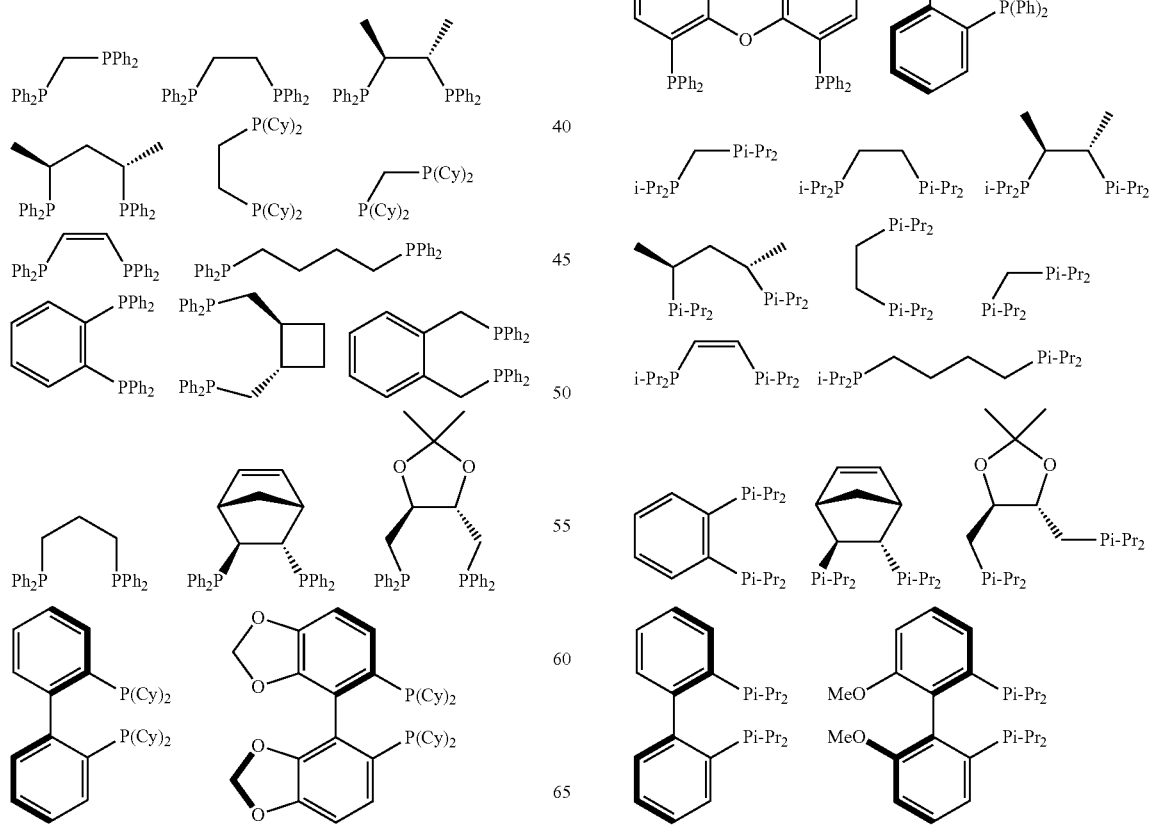

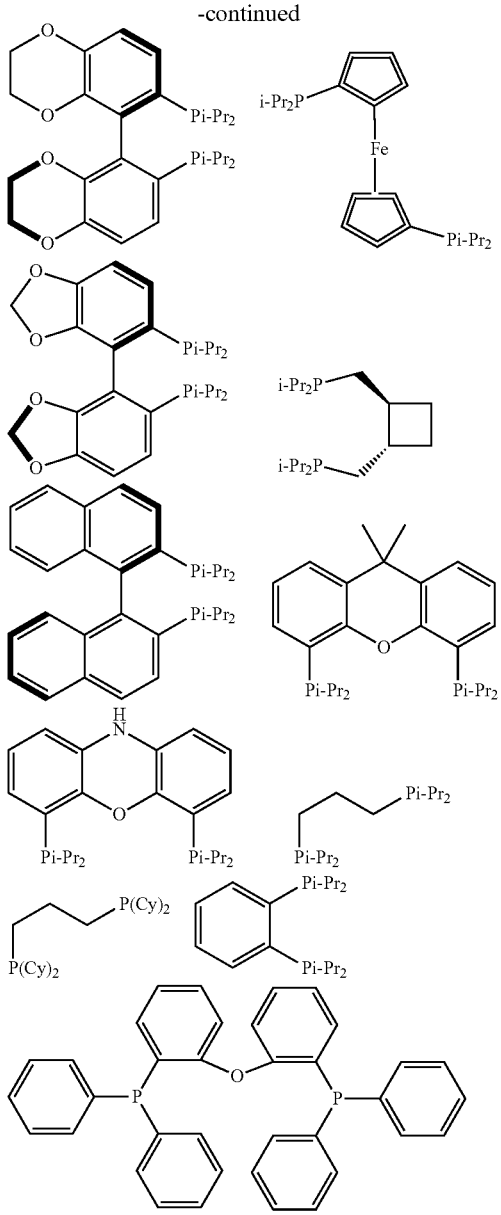

said compounds being in an optically active form or in a racemic form, if applicable, and wherein Ph represents a phenyl group, Cy represents a $C_{5-6}$ cycloalkyl group and i-Pr represents an iso-propyl group. It is also understood that in the above diphosphines, one may replace Cy group by a Ph group or vice versa.

Preferably, ligand (PP) may be selected from the group consisting of bis(dicyclohexylphophanyl)methane, 1,2-bis(dicyclohexylphosphanyl)ethane, 1,2-bis(diphenylphosphanyl)ethane, 1,2-bis(diphenylphosphanyl)ethane, 1,3-bis(diisopropylphosphanyl)propane, 1,4-bis(diphenylphosphanyl)butane, 1,1'-bis(diphenylphosphanyl)ferrocene, 1,1'-bis(diisopropylphosphanyl)ferrocene, 1,1'-bis(dicyclohexylphosphanyl)ferrocene, 2,2'-bis(diphenylphosphaneyl)-1,1'-biphenyl, 2,2'-bis(dicyclohexylphosphaneyl)-1,1'-biphenyl, (oxybis(2,1-phenylene))bis(diphenylphosphane) and 4,6-bis(diphenylphosphanyl)-10H-phenoxazine.

Preferably, ligand (PP) may be 1,2-bis(diphenylphosphanyl)ethane, 1,3-bis(diisopropylphosphanyl)propane, 1,3-bis(dicyclohexylphosphanyl)propane, 1,4-bis(diphenylphosphanyl)butane or 1,1'-bis(diphenylphosphanyl)ferrocene.

The ligands described above can be obtained by applying standard general methods which are well known in the state of the art and by the person skilled in the art. Many of said ligands NN or PP are even commercially available.

The complexes of formula (1) are generally prepared and isolated prior to their use in the process as exemplified in the Examples herein below but can also be generated directly in situ from the same precursor $[(COD)Ru(RCOO)_2]_n$ (described in the International application No PCT/IB2011/052108) using one equivalent of PP ligand and optionally one equivalent of NN ligand respect to ruthenium or from $(NN)(COD)Ru(RCOO)_2$ complexes using one equivalent of PP ligand respect to ruthenium. In addition, said complexes (1) can also be generated in situ from the known diamine diphosphine ruthenium complex derivatives (PP)(NN)Ru(X)(Y), X and Y being di-alkoxyde (di-isopropoxyde for example), hydridoborohydrido, cationic monoacetate or dicationic (or a mix of those) complexes by adding an excess of an acid RCOOH wherein R has the meaning provided in formula (1). The said complexes (1) can also be generated in situ from the known diamine diphosphine chlorinated ruthenium complex derivatives (PP)(NN)Ru(Cl)(Y) such as dichloride or cationic monochloride complexes by adding an excess of an acid RCOOH wherein R has the meaning provided in formula (1), optionally in the presence of a stoechiometric amount of a silver salt ($AgOCOCH_3$, $AgBF_4$, $AgPF_6$, $AgOSO_2CF_3$ for example) with respect to chloride atoms.

The processes may comprise the addition of a protic additive. Said additive has the astonishing effect of increasing the speed and sometimes also the yield of the reaction.

As non-limiting example, said protic additive may be selected amongst an alcohol of formula $R^{13}OH$, wherein $R^{13}$ is a C1-10 alkyl or alkenyl group optionally substituted by at least one fluorine atom.

As non-limiting examples of said protic additive, one may cite the following: ethanol, propanol, cyclohexanol, isopropanol or butanol.

As previously mentioned, the processes of the invention consist in the hydrogenation of a substrate using a ruthenium complex in the absence of an acid or a base. A typical process implies the mixture of the substrate with the ruthenium complex, and optionally a solvent and optionally a protic additive, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 1 ppm to 10000 ppm relative to the amount of substrate. Preferably, the complex concentration will be comprised between 10 ppm to 5000 ppm. Even more preferably, the complex concentration will be comprised between 100 ppm to 2500 ppm It goes without saying that the optimum concentration of complex will depend, as the person skilled in the art knows, on the nature of the latter, on the nature and quality of the substrate, on the nature of the solvent used if any, on the reaction temperature and on the pressure of $H_2$ used during the process, as well as the desired time of reaction.

Useful quantities of protic additive, added to the reaction mixture, may be comprised in a relatively large range. One can cite, as non-limiting examples, ranges between 1 to 10000 molar equivalents, relative to the complex of formula (1), preferably 10 to 2000 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include $C_{6-10}$ aromatic solvents such as toluene or xylene; $C_{5-12}$ hydrocarbon solvents such as hexane or cyclohexane; $C_{4-8}$ ethers such as tetrahydrofuran or MTBE; $C_{4-10}$ esters such as ethyl acetate; $C_{1-2}$ chlorinated hydrocarbon, such as dichloromethane; $C_{2-6}$ primary or secondary alcohols, such as isopropanol or ethanol; $C_{2-6}$ polar solvents such as acetone; or mixtures thereof. In particular said solvent can be a protic solvent such as isopropanol or ethanol. The choice of the solvent is a function of the nature of the complex and the substrate, and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 100 bars) or even more if desired. Again, a person skilled in the art is well able to adjust the pressure as a function of the catalyst load and of the dilution of the substrate in the solvent. As examples, one can cite typical pressures of 5 to $50 \times 10^5$ Pa (5 to 50 bars).

The temperature at which the hydrogenation can be carried out is comprised between 0° C. and 200° C., more preferably in the range of between 50° C. and 150° C. Of course, a person skilled in the art is also able to select the preferred temperature as a function of the melting and boiling point of the starting and final product as well as the desired time of reaction or conversion.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in stainless steel autoclave. $H_2$ gas (99.99990%) was used as received. NMR spectra were recorded on a Bruker AM-400 ($^1H$ at 400.1 MHz, $^{13}C$ {$^1H$} at 100.6 MHz, and $^{31}P$ at 161.9 MHz) spectrometer and normally measured at 300 K, in $CD_2Cl_2$ unless indicated otherwise. Chemical shifts are listed in ppm.

Example 1

Catalytic hydrogenation of imines using complex [Ru(OPiv)$_2$(PP)(en)] (OPiv=Pivalate, en=ethane-1,2-diamine) generated in-situ:

General procedure for the catalytic hydrogenation of (E)-N-(1H-pyrazol-5-yl)-1-(thiophen-2-yl)methanimine as substrate:

Under argon, a 10 ml vial was charged with [Ru(OPiv)$_2$(cod)]$_2$[H$_2$O] (3.3 mg, 0.004 mmoles, 0.25 mol %) and the corresponding diphosphine (0.009 mmoles, 0.3 mol %) followed by EtOH (2 ml). The vial was sealed and heated in an aluminium block at 50° C. for 3h. Then the vial was brought back under argon, and a solution of ethylene diamine in EtOH (1 ml at 0.0125 M, 0.0125 mmoles, 0.4 mol %) was added. The vial was sealed and heated again at 67° C. for 2h. Then the solution was added under argon into a glass tube containing the imine (3 mmol), and the tube was placed in a *Biotage Endeavour®* multi-reactor. The tube was pressurised with hydrogen gas at 30 bar and heated at 100° C. with stirring (800 rpm). After 20 h, the system was cooled to room temperature and ventilated.

Then, an aliquot (0.1 ml) was taken, diluted with $CH_2Cl_2$ (1 ml) and analysed by GC (HP-1).

The results with various diphosphines taken from Table 2 are shown in Table 1.

TABLE 1

Hydrogenation of (E)-N-(1H-pyrazol-5-yl)-1-(thiophen-2-yl)methanimine using [Ru(OPiv)$_2$(PP)(en)] generated in-situ:

| Test | PP[a] | Ru[b] | Conv.[c] | Amine[d] |
|------|-------|-------|----------|----------|
| 1 | L1 | 1000 | 100 | 99 |
| 2 | L1 | 500 | 60 | 40 |
| 3 | L2 | 2500 | 100 | 99 |
| 4 | L2 | 1000 | 100 | 96 |
| 5 | L2 | 500 | 75 | 55 |
| 6 | L3 | 2500 | 100 | 95 |
| 7 | L3 | 1000 | 100 | 96 |
| 8 | L3 | 500 | 100 | 93 |
| 9 | L4 | 2500 | 100 | 93 |
| 10 | L4 | 1000 | 100 | 96 |
| 11 | L4 | 500 | 100 | 100 |
| 12 | L5 | 2500 | 100 | 97 |
| 13 | L5 | 1000 | 100 | 97 |
| 14 | L5 | 500 | 100 | 92 |
| 15 | L6 | 2500 | 100 | 95 |
| 16 | L6 | 1000 | 100 | 97 |
| 17 | L6 | 500 | 100 | 93 |
| 18 | L7 | 2500 | 100 | 83 |

[a] Diphosphines used as described in Table 2.
[b] Molar ratio in ppm of complex relative to the substrate.
[c] Conversion calculated according to amount of starting material left as measured by GC (HP-1).
[d] Amount of desired amine as measured by GC (HP-1).

TABLE 2

Structure and names of diphosphines used

| Ligand | Structure | Name |
|--------|-----------|------|
| L1 | 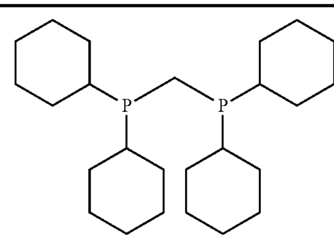 | bis(dicyclohexylphosphanyl)methane |

TABLE 2-continued
Structure and names of diphosphines used
| Ligand | Structure | Name |
|---|---|---|
| L2 | 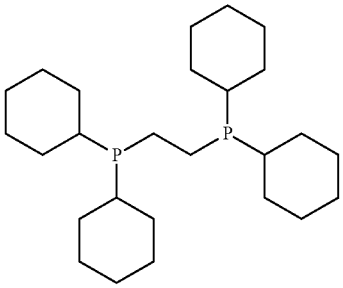 [SMILES: C1CCC(P(CCP(C2CCCCC2)C2CCCCC2)C2CCCCC2)CC1] | 1,2-bis(dicyclohexylphosphanyl)ethane |
| L3 | 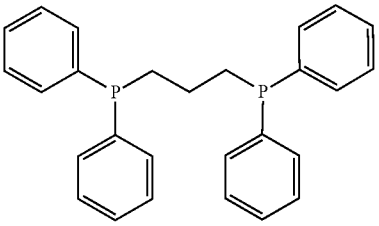 [SMILES: c1ccc(P(CCCP(c2ccccc2)c2ccccc2)c2ccccc2)cc1] | 1,2-bis(diphenylphosphanyl)ethane |
| L4 | 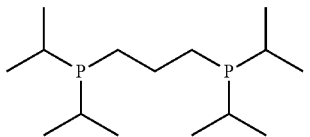 [SMILES: CC(C)P(CCCP(C(C)C)C(C)C)C(C)C] | 1,3-bis(diisopropylphosphanyl)propane |
| L5 | 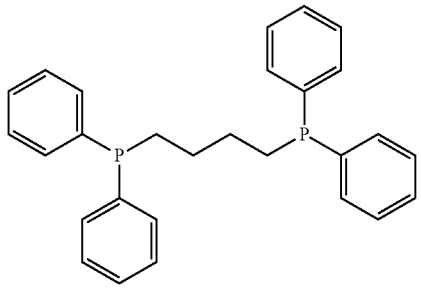 [SMILES: c1ccc(P(CCCCP(c2ccccc2)c2ccccc2)c2ccccc2)cc1] | 1,4-bis(diphenylphosphanyl)butane |
| L6 | 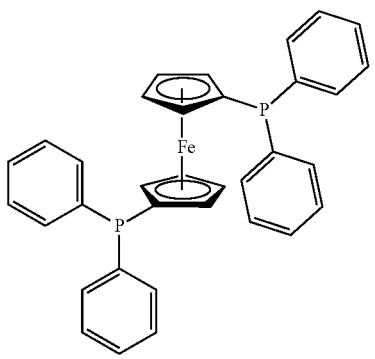 | 1,1'-bis(diphenylphosphanyl)ferrocene |

TABLE 2-continued

Structure and names of diphosphines used

| Ligand | Structure | Name |
| --- | --- | --- |
| L7 | 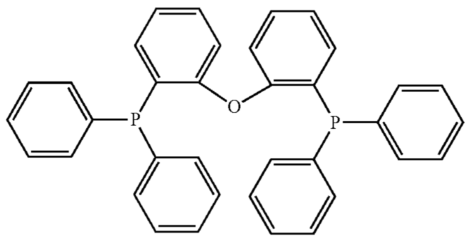 [SMILES: c1ccc(P(c2ccccc2)c2ccccc2Oc2ccccc2P(c2ccccc2)c2ccccc2)cc1] | (oxybis(2,1-phenylene))bis(diphenylphosphane) |
| L8 | 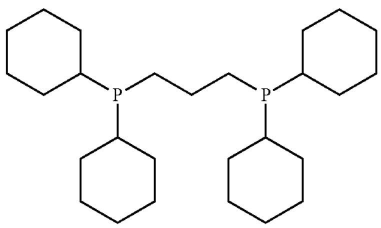 [SMILES: C1CCC(P(CCCP(C2CCCCC2)C2CCCCC2)C2CCCCC2)CC1] | 1,3-bis(dicyclohexylphosphanyl)propane |

Example 2

Catalytic hydrogenation of imines using complex [Ru(OPiv)$_2$(PP)(NN)] (OPiv=Pivalate) generated in-situ:

General procedure for the catalytic hydrogenation of (E)-N-(1H-pyrazol-5-yl)-1-(thiophen-2-yl)methanimine as substrate:

Under argon, a 10 ml vial was charged with the preformed [Ru(OPiv)$_2$(L4)] (4.5 mg, 0.006 mmoles) followed by a solution of the corresponding diamine in EtOH (1 ml at 0.07 M, 0.007 mmoles). More EtOH (1 ml) was added and the vial was sealed and heated in an aluminium block at 60° C. for 1.5h. Then a part (0.2 ml, 0.0006 mmoles, 0.02 mol %) of this solution was added to a glass tube containing the imine (3 mmol). More EtOH (2.8 ml) was added and the tube was placed in a *Biotage Endeavour*® multi-reactor. The tube was pressurised with hydrogen gas at 30 bar and heated at 100° C. with stirring (800 rpm). After 16 hours, the system was cooled to room temperature and ventilated. Then, an aliquot (0.1 ml) was taken, diluted with CH$_2$Cl$_2$ (1 ml) and analysed by GC (HP-1). The results with various ruthenium complexes and various diamines taken from Table 4 are shown in Table 3.

TABLE 3

Hydrogenation of (E)-N-(1H-pyrazol-5-yl)-1-(thiophen-2-yl)methanimine using [Ru(OPiv)$_2$(PP)(NN)] generated in-situ:

| Test | PP[a] | NN[b] | Ru[c] | Conv.[d] | Amine[e] |
| --- | --- | --- | --- | --- | --- |
| 1 | L3 | N1 | 200 | 100 | 89 |
| 2 | L3 | N2 | 200 | 100 | 95 |
| 3 | L3 | N3 | 200 | 100 | 84 |
| 4 | L3 | N4 | 200 | 96 | 76 |
| 5 | L3 | N5 | 200 | 100 | 89 |
| 6 | L3 | N6 | 200 | 79 | 56 |
| 7 | L3 | N7 | 200 | 100 | 94 |
| 8 | L4 | N1 | 200 | 100 | 99 |
| 9 | L4 | N2 | 200 | 100 | 97 |
| 10 | L4 | N3 | 200 | 100 | 97 |
| 11 | L4 | N4 | 200 | 100 | 98 |
| 12 | L4 | N5 | 200 | 100 | 98 |
| 13 | L4 | N6 | 200 | 99 | 97 |
| 14 | L4 | N7 | 200 | 99 | 95 |

[a] Diphosphines used as described in Table 2.
[b] Diamines used as described in Table 4.
[c] Molar ratio in ppm of complex relative to the substrate.
[d] Conversion calculated according to amount of starting material left as measured by GC (HP-1).
[e] Amount of desired amine as measured by GC (HP-1).

TABLE 4

Structure and names of diamines used.

| Ligand | Structure | Name |
| --- | --- | --- |
| N1 | 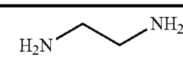 | ethane-1,2-diamine |
| N2 | 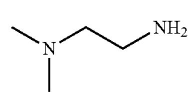 | N,N-dimethylethane-1,2-diamine |
| N3 | 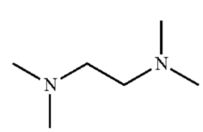 | N,N,N',N'-tetramethylethane-1,2-diamine |
| N4 | 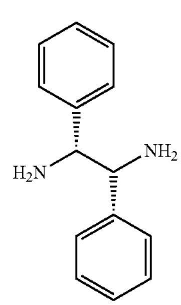 | (1R,2R)-1,2-diphenylethane-1,2-diamine |

TABLE 4-continued

Structure and names of diamines used.

| Ligand | Structure | Name |
|---|---|---|
| N5 | (structure: cyclohexane with H2N and NH2) | (1R,2R)-cyclohexane-1,2-diamine |
| N6 | (structure: pyridine-CH2-NH2) | pyridin-2-ylmethanamine |
| N7 | H2N~~~NH2 | propane-1,3-diamine |

Example 3

Catalytic hydrogenation of imines using complex [Ru(OPiv)$_2$(L4)(N1)] (OPiv=Pivalate):

General procedure for the catalytic hydrogenation of (E)-N-(1H-pyrazol-5-yl)-1-(thiophen-2-yl)methanimine as substrate:

A 500 ml stainless steel autoclave was charged with preformed [Ru(OPiv)$_2$(L4)(N1)] (18.6 mg, 0.029 mmoles), (E)-N-(1H-pyrazol-5-yl)-1-(thiophen-2-yl)methanimine (25.2 g, 142 mmoles) and absolute EtOH (88.2 g). The autoclave was closed, purged with hydrogen gas (5×10 bar) and then pressurized at 15 bar. The reaction was stirred (800 rpm) and heated at 100° C. After 7.5 h the autoclave was cooled to room temperature. The reaction mixture was removed from the autoclave and some EtOH was added to rinse the autoclave. A sample (10.9 g) of the reaction mixture (137.7 g) was concentrated under vacuum (35 mbar/40° C.) to give a brown oil (2.42 g), which was distilled on a Kugel-Rohr (0.4 mbar/208-224° C.) to give a colourless oil (1.93 g) with some residue left (0.15 g), which corresponded to an extrapolated yield of 96%.

The results at various temperature and hydrogen gas pressure are shown in Table 5.

TABLE 5

Hydrogenation of (E)-N-(1H-pyrazol-5-yl)-1-(thiophen-2-yl)methanimine using preformed [Ru(OPiv)$_2$(L4)(N1)] complexes at various temperature and pressure:

| Test | T[° C.] | H$_2$ [bar] | Ru[a] | Time [h] | Conv.[b] | Amine[c] | Yield[d] |
|---|---|---|---|---|---|---|---|
| 1 | 100 | 15 | 200 | 7.5 | 100 | 99 | 96 |
| 2 | 100 | 26 | 200 | 8 | 100 | 99 | — |
| 3 | 90 | 15 | 200 | 10.5 | 99.5 | 97 | 96 |
| 4 | 110 | 15 | 200 | 5.5 | 100 | 96 | — |

[a] Molar ratio in ppm of complex relative to the substrate.
[b] Conversion calculated according to amount of starting material left as measured by GC (HP-1).
[c] Amount of desired amine as measured by GC (HP-1).
[d] Isolated yield after distillation.

Example 4

Catalytic hydrogenation of imines using complex [Ru(OPiv)$_2$(L4)] (OPiv=Pivalate):

General procedure for the catalytic hydrogenation of (E)-N-(1H-pyrazol-5-yl)-1-(thiophen-2-yl)methanimine as substrate:

A 500 ml stainless steel autoclave was charged with preformed [Ru(OPiv)$_2$(L4)] (34.1 mg, 0.059 mmoles), (E)-N-(1H-pyrazol-5-yl)-1-(thiophen-2-yl)methanimine (50.5 g, 285 mmoles) and absolute EtOH (175.1 g). The autoclave was closed, purged with hydrogen gas (5×10 bar) and then pressurized at 25 bar. The reaction was stirred (800 rpm) and heated at 100° C. After 8 h the autoclave was cooled to room temperature. The reaction mixture was removed from the autoclave and some EtOH was added to rinse the autoclave. A sample (10.6 g) of the reaction mixture (259.6 g) was concentrated under vacuum (20 mbar/40° C.) to give a brown oil (2.31 g), which was distilled on a Kugel-Rohr (0.2 mbar/180-215° C.) to give a colourless oil (1.93 g) with some residue left (0.12 g), which corresponded to an extrapolated yield of 92%.

Example 5

Catalytic Hydrogenation of imines using Complex [Ru(OPiv)$_2$(L4)(N1)] (OPiv=Pivalate):

General procedure for the catalytic hydrogenation of various imines taken from Table 6. A glass tube is charged with [Ru(OPiv)$_2$(L4)(N1)] (9.9 mg, 0.015 mmoles, 0.5 mol %), (E)-N-(4-methoxyphenethyl)-1-(thiophen-2-yl)methanimine (738.8 mg, 3 mmoles) and absolute EtOH (3 ml). The tube was then placed in a *Biotage Endeavour®* multi-reactor, and pressurised with hydrogen gas at 15 bar and heated at 100° C. with stirring (800 rpm). After 16 h, the system was cooled to room temperature and ventilated. Then, an aliquot (0.1 ml) was taken, diluted with CH$_2$Cl$_2$ (1 ml) and analysed by GC (HP-1). Purification by column chromatography (SiO$_2$, CH$_2$Cl$_2$/Et$_2$O 4/1+Et$_3$N 1%) gave the desired product (500 mg, 1.99 mmoles, 66%).

Using these conditions several imines described in Table 6 were hydrogenated and the results are shown in Table 7.

TABLE 6

Structure and names of imines hydrogenated.

| Ligand | Structure | Name |
|---|---|---|
| S1 | (pyrazole-N=CH-thiophene structure) | (E)-N-(1H-pyrazol-5-yl)-1-(thiophen-2-yl)methanimine |

TABLE 6-continued

Structure and names of imines hydrogenated.

| Ligand | Structure | Name |
|---|---|---|
| S2 | 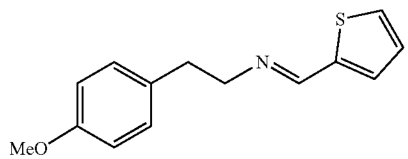 [SMILES: COc1ccc(CC/N=C/c2cccs2)cc1] | (E)-N-(4-methoxyphenethyl)-1-(thiophen-2-yl)methanimine |
| S3 | 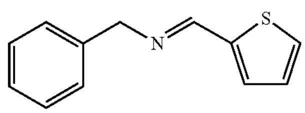 [SMILES: C(=N\Cc1ccccc1)/c1cccs1] | (E)-N-benzyl-1-(thiophen-2-yl)methanimine |
| S4 | 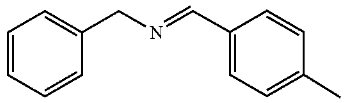 [SMILES: Cc1ccc(/C=N/Cc2ccccc2)cc1] | (E)-N-benzyl-1-(p-tolyl)methanimine |
| S5 | 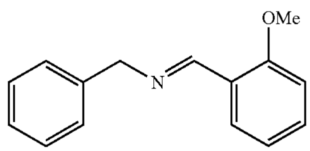 [SMILES: COc1ccccc1/C=N/Cc1ccccc1] | (E)-N-benzyl-1-(2-methoxyphenyl)methanimine |
| S6 | 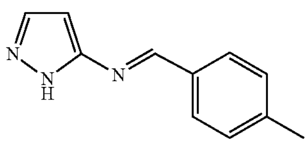 | (E)-N-(1H-pyrazol-5-yl)-1-(p-tolyl)methanimine |

TABLE 7

Hydrogenation of imines described in Table 6 using [Ru(OPiv)$_2$(L4)(N1)]:

| Test | Imines | Ru[a] | Conv.[b] | Amine[c] | Yield[d] |
|---|---|---|---|---|---|
| 1 | S2 | 5000 | 99 | 85 | 66 |
| 2 | S3 | 5000 | 89 | 74 | 64 |
| 3 | S4 | 5000 | 98 | 84 | 79 |
| 4 | S5 | 5000 | 95 | 77 | 68 |
| 5[e] | S6 | 5000 | 100 | 91 | 76 |

[a] Molar ratio in ppm of complex relative to the substrate.
[b] Conversion calculated according to the amount of starting material left as measured by GC (HP-1).
[c] Amount of desired amine as measured by GC (HP-1).
[d] Isolated yield after purification.
[e] Test performed in THF.

Example 6

Comparative Example—Catalytic Hydrogenation of imines using Complex [Ru(bis(2-(diphenylphosphaneyflethyl)amine)(CO)(H)(BH$_4$)]:

General procedure for the catalytic hydrogenation of (E)-N-(1H-pyrazol-5-yl)-1-(thiophen-2-yl)methanimine as substrate in various solvents:

Under argon, a 10 ml tube was charged with [Ru(bis(2-(diphenylphosphaneyl)ethyDamine)(CO)(H)(BH$_4$)] (12.9 mg, 0.022 mmoles, 1.1 mol %), (E)-N-(1H-pyrazol-5-yl)-1-(thiophen-2-yl)methanimine (355.6 mg, 2.01 moles) and THF (3 ml). The tube was placed in a *Biotage Endeavour®* multi-reactor. The tube was pressurised with hydrogen gas at 20 bar and heated at 100° C. with stirring (800 rpm). After 20 h, the system was cooled to room temperature and ventilated. Then, an aliquot (0.1 ml) was taken, diluted with CH$_2$Cl$_2$ (1 ml) and analysed by GC (HP-1). The results with various solvents are shown in Table 8.

TABLE 8

Hydrogenation of (E)-N-(1H-pyrazol-5-yl)-1-(thiophen-2-yl)methanimine using [Ru(bis(2-(diphenylphosphaneyl)ethyl)amine)(CO)(H)(BH$_4$)] in various solvent:

| Test | Solvent | Conv.[a] | Amine[b] |
|---|---|---|---|
| 1 | THF | 6 | 2 |
| 2 | Toluene | 13 | 3 |
| 3 | MTBE | 12 | 3 |
| 4 | iPrOH | 6 | 6 |
| 5 | EtOH | 8 (20[c]) | 7 (13[c]) |
| 6 | MeOH | 10 | 6 |

[a] Conversion calculated according to the amount of starting material left as measured by GC (HP-1).
[b] Amount of desired amine as measured by GC (HP-1).
[c] Test performed with H$_2$ (80 bar) at 100° C. for 20 h.

Example 7

Catalytic Hydrogenation of imines using Complex [Ru(OPiv)$_2$(L8)] (OPiv=Pivalate):

General procedure for the catalytic hydrogenation of various imines taken from Table 9. A stainless steel autoclave of 60 ml is charged with [Ru(OPiv)$_2$(L8)] (40.4 mg, 0.055 mmoles, 0.5 mol %), (E)-N-phenyl-1-(2-thienyl)methanimine (2.048 g, 10.94 mmoles) and MeOH (9 ml). The autoclave was closed and pressurised with hydrogen gas at 50 bar and heated at 100° C. with stirring (800 rpm). After 26 h, the system was cooled to room temperature and ventilated. Then, the reaction mixture was concentrated under vacuum (40° C./5 mbar) to give a brown oil (2.089 g).

Analysis by ¹H-NMR showed complete conversion. Purification by Kugel-Rohr distillation (bp: 160-170° C./0.4 mbar) gave a white solid (1.855 g, GC (HP-1): 99.5%, 89% yield).

Using these conditions several imines described in Table 9 were hydrogenated and the results are shown in Table 10.

TABLE 9

Structure and names of imines hydrogenated.

| Ligand | Structure | Name |
|---|---|---|
| S7 | 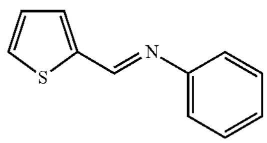 [SMILES: C(=N\c1ccccc1)/c1cccs1] | (E)-N-phenyl-1-(thiophen-2-yl)methanimine |
| S8 | 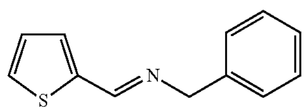 [SMILES: C(=N\Cc1ccccc1)/c1cccs1] | (E)-N-benzyl-1-(thiophen-2-yl)methanimine |
| S9 | 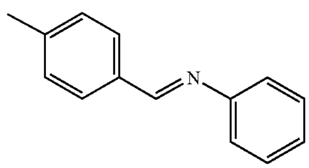 | (E)-N-phenyl-1-(p-tolyl)methanimine |
| S10 | 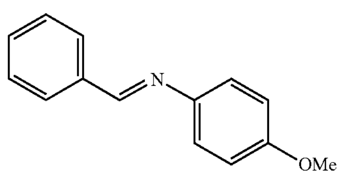 [SMILES: COc1ccc(/N=C/c2ccccc2)cc1] | (E)-N-(4-methoxyphenyl)-1-phenylmethanimine |
| S11 | 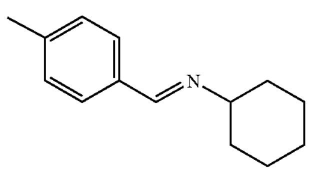 | (E)-N-cyclohexyl-1-(p-tolyl)methanimine |
| S12 | 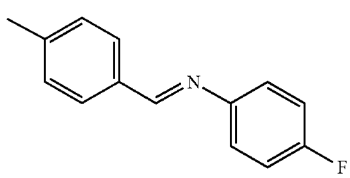 [SMILES: Cc1ccc(/C=N/c2ccc(F)cc2)cc1] | (E)-N-(4-fluorophenyl)-1-(p-tolyl)methanimine |
| S13 | 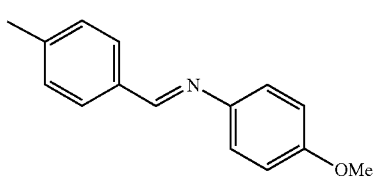 [SMILES: COc1ccc(/N=C/c2ccc(C)cc2)cc1] | (E)-N-(4-methoxyphenyl)-1-(p-tolyl)methanimine |
| S14 | 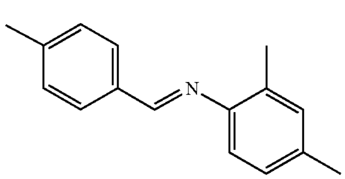 | (E)-N-(2,4-dimethylphenyl)-1-(p-tolyl)methanimine |

TABLE 9-continued

Structure and names of imines hydrogenated.

| Ligand | Structure | Name |
|---|---|---|
| S15 | 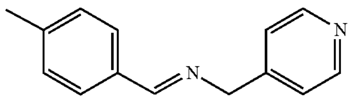 [SMILES: Cc1ccc(/C=N/Cc2ccncc2)cc1] | (E)-N-(pyridin-4-ylmethyl)-1-(p-tolyl)methanimine |
| S16 | 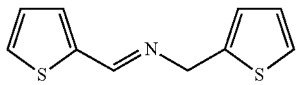 [SMILES: C(=N\Cc1cccs1)/c1cccs1] | (E)-1-(thiophen-2-yl)-N-(thiophen-2-ylmethyl)methanimine |

TABLE 10

Hydrogenation of imines described in Table 9 using [Ru(OPiv)$_2$(L8)]:

| Test | Imines | Ru[a] | Time (h) | Conv.[b] | Yield[c] |
|---|---|---|---|---|---|
| 1 | S7 | 5000 | 26 | 100 | 89 |
| 2 | S8 | 5000 | 24 | 100 | 90 |
| 3 | S9 | 5000 | 38.5 | 100 | 97 |
| 4 | S10 | 5000 | 38.5 | 100 | 90 |
| 5 | S11 | 5000 | 24 | 100 | 93 |
| 6 | S4 | 5000 | 24 | 100 | 89 |
| 7 | S12 | 5000 | 24 | 100 | 97 |
| 8 | S13 | 5000 | 24.5 | 100 | 96 |
| 9 | S14 | 5000 | 25 | 100 | 88 |
| 10 | S15 | 5000 | 24 | 100 | 70 |
| 11 | S16 | 5000 | 24 | 100 | 83 |

[a]Molar ratio in ppm of complex relative to the substrate.
[b]Conversion calculated according to the amount of starting material left as measured by GC (HP-1) in the crude reaction mixture.
[c]Isolated yield after Kugel-Rohr distillation of the desired amine.

Example 8

Comparative Example—Catalytic Hydrogenation of (E)-N-(1H-pyrazol-5-yl)-1-(thiophen-2-yl)methanimine as Substrate using Various ruthenium Complexes with and without Base General Procedure for the Catalytic Hydrogenation:

A 10 ml glass tube was charged with [Ru(OPiv)$_2$(L3)(N4)] (1.4 mg, 0.015 mmoles, 0.1 mol %), (E)-N-(1H-pyrazol-5-yl)-1-(thiophen-2-yl)methanimine (266.6 mg, 1.5 mmoles) and absolute EtOH (3 ml). The tube was then placed in a *Biotage Endeavour*® multi-reactor, and pressurised with hydrogen gas at 10 bar and then heated at 100° C. with stirring (800 rpm). After 12 h, the system was cooled to room temperature and ventilated. Then, an aliquot (0.1 ml) was taken, diluted with CH$_2$Cl$_2$ (1 ml) and analysed by GC (HP-1). Using these conditions several ruthenium complexes were compared and the results are shown in Table 11.

TABLE 11

Hydrogenation of (E)-N-(1H-pyrazol-5-yl)-1-(thiophen-2-yl)methanimine using various ruthenium complexes in ethanol:

| Test | Ruthenium complexes | Base (mol %) | Conv.[a] | Amine[b] |
|---|---|---|---|---|
| 1 | [Ru(OPiv)$_2$(L3)(N4)] | — | 27 | 23 |
| 2 | [Ru(Cl)$_2$(L3)(N4)][c] | tBuOK (10) | 3 | 1 |

[a]Conversion calculated according to the amount of starting material left as measured by GC (HP-1).
[b]Amount of desired amine as measured by GC (HP-1).
[c]Comparative example; complex not part of the invention When the hydrogenation was carried out with [Ru(Cl)$_2$(L3)(N4)] in a presence of base, as reported in prior art, only 1% of amine was detected after 12h (Table 11, entry 2). In the same conditions, with the invention's complex, 23% of amine was detected (Table 11, entry 1). The hydrogenation of the present invention allows improving the hydrogenation of amine.

The invention claimed is:

1. A process for the reduction by hydrogenation, using molecular H$_2$, of a C$_5$-C$_{20}$ substrate of formula

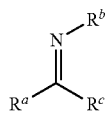

(I)

wherein R$^a$ and R$^c$ represent, independently from each other, a hydrogen atom or a C$_1$-C$_{15}$ hydrocarbon group optionally comprising one to three oxygen atoms and/or one to two nitrogen atoms and/or one sulphur or halogen atom; R$^b$ represents a C$_1$-C$_{15}$ hydrocarbon group optionally comprising one to three oxygen atoms and/or one to two nitrogen atoms and/or one sulphur or halogen atom, a hydrogen atom, a SO$_2$R$^{b'}$, a OR$^{b''}$ or a POR$^{b'}$$_2$ group wherein R$^{b'}$ represents a C$_1$-C$_6$ alkyl group or a phenyl or tolyl group and R$^{b''}$ represents a hydrogen atom, a C$_1$-C$_6$ alkyl group or a phenyl or tolyl group; or R$^a$ and R$^c$ represent, when taken together, a C$_1$-C$_{10}$ alkanediyl or alkenediyl group; provided that at least one R$^a$, R$^b$, or R$^c$ is not a hydrogen atom;

into the corresponding amine, wherein said process is carried out in the presence of at least one catalyst or pre-catalyst of formula

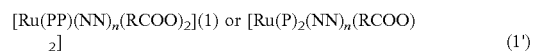

(1')

wherein n is 0 or 1;
PP represents a C$_5$-C$_{50}$ bidentate ligand wherein the coordinating groups are two phosphino groups;
P represents a C$_3$-C$_{50}$ monodentate ligand;
NN represents a C$_2$-C$_{20}$ bidentate ligand wherein the coordinating atoms are two nitrogen atoms; and
each R represents, simultaneously or independently, a hydrogen atom, a C$_1$-C$_{12}$ linear hydrocarbon group, or a branched or cyclic C$_3$-C$_{12}$ hydrocarbon group and said hydrocarbon group comprises optionally one to five heteroatoms selected amongst halogen, oxygen and nitrogen atoms; and wherein the process is performed in the absence of a base additive.

2. The process according to claim 1, wherein $R^a$, $R^b$ and $R^c$ represent, independently from each other, a hydrogen atom, a $C_1$-$C_{10}$ linear alkyl group, a $C_2$-$C_{10}$ linear alkenyl group, a $C_3$-$C_{10}$ linear, branched, or cyclic alkyl or alkenyl group, a $C_4$-$C_{10}$ linear, branched, or cyclic alkadienyl group, a $C_{3-8}$ aryl, a $C_{2-8}$ heterocyclic, or a $C_{6-12}$ arylalkyl group optionally substituted by a hydroxyl group, a $C_{1-6}$ alkyl group or a $C_{1-6}$ alkoxy group; or $R^a$ and $R^c$ represent, when taken together, a $C_1$-$C_{10}$ alkanediyl or alkenediyl group; provided that at least one $R^a$, $R^b$, or $R^c$ is not a hydrogen atom.

3. The process according to claim 1, wherein $R^c$ is a hydrogen atom.

4. The process according to claim 1, wherein $R^a$ or $R^b$ represent a $C_{2-6}$ heterocyclic group optionally substituted by a hydroxyl group, a $C_{1-3}$ alkyl group, or a $C_{1-3}$ alkoxy group and the other represents a $C_1$-$C_8$ linear alkyl group, a $C_2$-$C_8$ linear alkenyl group, a $C_3$-$C_8$ linear, branched, or cyclic alkyl or alkenyl group, a $C_4$-$C_8$ linear, branched, or cyclic alkadienyl group, or a $C_{3-6}$ aryl, $C_{2-6}$ heterocyclic, or $C_{6-8}$ arylalkyl group optionally substituted by a hydroxyl group, a $C_{1-3}$ alkyl group, or a $C_{1-3}$ alkoxy group.

5. The process according to claim 1, wherein $R^a$ and $R^b$ represent, independently from each other, a $C_{3-6}$ heterocyclic group comprising from 1 to 3 heteroatoms selected from nitrogen, oxygen, and sulphur.

6. The process according to claim 1, wherein the catalyst or the pre-catalyst is of formula

wherein PP, NN, R, and n have the same meaning as defined in claim 1.

7. The process according to claim 6, wherein the RCOO group of (I) is selected from the group consisting of isobutyrate, pivalate, $^t$Bu-acetate, trifluoroacetate, 2-Et-hexanoate, cyclohexanecarboxylate, picolinate, cinnamate, benzoate, 4-Me-benzoate, 4-OMe-benzoate, 3,5-dichloro-benzoate, 2,4-dichloro-benzoate, isovalerate, adamantate, and sec-butyrate.

8. The process according to claim 1, wherein the bidentate NN ligand is a compound of formula

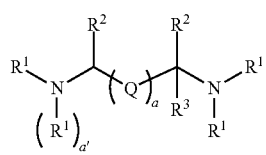

wherein a and a', simultaneously or independently, represent 0 or 1, when a' is 0 then the nitrogen atom is part of an aromatic heterocycle;

the $R^1$, taken separately, represent, simultaneously or independently, a hydrogen atom or a $C_{1-6}$ linear, branched, or cyclic alkyl group optionally substituted or a phenyl or a benzyl group optionally substituted; two $R^1$, taken together, may form a saturated heterocycle containing 3 to 7 atoms and including the atoms to which said 1e are bonded, said heterocycle being optionally substituted;

$R^2$ and $R^3$, taken separately, represent, simultaneously or independently, a hydrogen atom, a $C_{1-6}$ linear, branched alkyl group optionally substituted, or a $C_{6-10}$ aromatic group optionally substituted; a $R^1$ and an adjacent $R^2$, taken together, may form a saturated or unsaturated heterocycle containing 5 to 8 atoms and including the atoms to which said $R^1$ and $R^2$ are bonded, and optionally containing one additional nitrogen or oxygen atom; two $R^2$, taken together, may form a saturated or unsaturated ring having 5 to 8 atoms and including the carbon atoms to which said two $R^2$ groups are bonded, said ring optionally containing one additional nitrogen and/or oxygen atom; and Q represents a group of formula

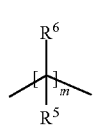

wherein m is 1 or 2, and $R^5$ and $R^6$ represent, simultaneously or independently, a hydrogen atom, a $C_{1-6}$ linear, branched, or cyclic alkyl group optionally substituted or a $C_{6-10}$ aromatic group optionally substituted; two distinct $R^6$ and/or $R^5$ groups, taken together, may form a $C_{3-8}$ saturated ring optionally substituted, including the atoms to which said $R^6$ and/or $R^5$ groups are bonded, and optionally containing one or two additional nitrogen or oxygen atoms.

9. The process according to claim 8, wherein a is 0.

10. The process according to claim 8, wherein the bidentate (NN) ligand is selected from the group consisting of ethane-1,2-diamine, N,N-dimethylethane-1,2-diamine, N,N,N',N'-tetramethylethane-1,2-diamine, 1,2-diphenylethane-1,2-diamine, (1R,2R)-1,2-diphenylethane-1,2-diamine, cyclohexane-1,2-diamine, (1R,2R)-cyclohexane-1,2-diamine, propane-1,3-diamine, and pyridin-2-ylmethanamine.

11. The process according to claim 1, wherein the bidentate ligand (PP) is a compound of formula

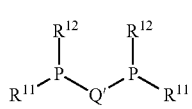

wherein $R^{11}$ and $R^{12}$, when taken separately, represent, simultaneously or independently, a $C_{1-6}$ linear alkyl group optionally substituted, a $C_{3-6}$ branched or cyclic alkyl group optionally substituted, or a $C_{6-10}$ aromatic group optionally substituted; and Q' represents
a group of formula

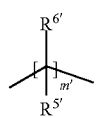

wherein m' is 1, 2, 3 or 4; and
$R^{5'}$ and $R^{6'}$ represent, simultaneously or independently, a hydrogen atom, a $C_{1-6}$ linear or branched alkyl group optionally substituted or a $C_{6-10}$ aromatic group optionally substituted; two distinct $R^{6'}$ and/or $R^{5'}$ groups, taken together, may form a $C_3$ to $C_8$ saturated or unsaturated ring optionally substituted, including the atoms to which said R$^{6'}$ and/or R$^{5'}$ groups are bonded, and optionally containing one or two additional nitrogen or oxygen atoms; or a C$_{10}$-C$_{16}$ metallocenediyl, a 2,2'-diphenyl, a 1,1'-binaphthalene-2,2'-diyl, a benzenediyl, a naphthalenediyl, 2,3-bicyclo[2:2:1]hept-5-enediyl, 4,6-phenoxazinediyl, 4,5-(9, 9-dimethyl)-xanthenediyl, 4,6-10H-phenoxazinediyl, 2,2'-(oxybis(2, 1-phenylene)), or bis(phen-2-yl)ether group optionally substituted.

12. The process according to claim 11, wherein the R$^{11}$ and R$^{12}$, when taken separately, represent, simultaneously or independently, a C$_{3-6}$ branched or cyclic alkyl group or a C$_{6-10}$ aromatic group.

13. The process according to claim 11, wherein the Q' represents a linear C$_{1-4}$ alkanediyl radical, a 1,2- or 1,1'-C$_{10-12}$ metallocenediyl, a 2,2'-diphenyl, a 1,2-benzenediyl, a 1,1'-binaphthalene-2,2'-diyl, or a 1,8- or 1,2-naphthalenediyl, 4,6-10H-phenoxazinediyl or 2,2'-(oxybis(2,1-phenylene)) group optionally substituted.

14. The process according to claim 11, wherein the (PP) ligand is selected from the group consisting of bis(dicyclohexylphosphanyl)methane, 1,2-bis(dicyclohexylphosphanyl)ethane, 1,2-bis(diphenylphosphanyl)ethane, 1,2-bis(diphenylphosphanyl)ethane, 1,3-bis(diisopropylphosphanyl)propane, 1,3-bis(dicyclohexylphosphanyl)propane, 1,4-bis(diphenylphosphanyl)butane, 1,1'-bis(diphenylphosphanyl)ferrocene, 1,1'-bis(dii sopropylphosphanyl)ferrocene, 1,1'-bis(dicyclohexylphosphanyl)ferrocene, 2,2'-bis(diphenylphosphaneyl)-1,1'-biphenyl, 2,2'-bis(dicyclohexylphosphaneyl)-1,1'-biphenyl, (oxybis(2,1-phenylene))bis(diphenylphosphane), and 4, 6-bis(diphenylphosphanyl)-10H-phenoxazine.

15. The process according to claim 1, wherein the complexes of formula (1) are generated directly in situ.

\* \* \* \* \*